(12) United States Patent
Tashiro et al.

(10) Patent No.: US 6,855,541 B2
(45) Date of Patent: Feb. 15, 2005

(54) KIT USED FOR FABRICATING AN INTEGRATED BIOMOLECULE SENSOR

(75) Inventors: Hideo Tashiro, Tokyo (JP); Yasumitsu Kondoh, Niiza (JP); Tokuji Kitsunai, Saitama (JP); Tomoko Tashiro, Tokyo (JP)

(73) Assignee: Riken (JP)

( * ) Notice: Subject to any disclaimer, the term of this patent is extended or adjusted under 35 U.S.C. 154(b) by 0 days.

(21) Appl. No.: 10/676,241

(22) Filed: Oct. 1, 2003

(65) Prior Publication Data

US 2004/0096962 A1 May 20, 2004

Related U.S. Application Data

(62) Division of application No. 09/962,434, filed on Sep. 25, 2001.

(30) Foreign Application Priority Data

Sep. 26, 2000 (JP) ........................................ 2000-292832

(51) Int. Cl.[7] .............................................. C12M 1/34
(52) U.S. Cl. ............................... 435/288.4; 435/288.7; 435/810
(58) Field of Search .......................... 435/287.2, 288.4, 435/288.7, 810

(56) References Cited

U.S. PATENT DOCUMENTS

| 6,023,540 | A | * | 2/2000 | Walt et al. | .................... | 385/12 |
| 6,406,845 | B1 | * | 6/2002 | Walt et al. | .................... | 435/6 |
| 2003/0143725 | A1 | * | 7/2003 | Chen et al. | ............... | 435/287.2 |

FOREIGN PATENT DOCUMENTS

| JP | 5-28500 | 11/1993 |
| WO | WO 97/27326 | 7/1997 |

OTHER PUBLICATIONS

U.S. Provisional Appl. No. 60/216,265, filed Jul. 2000, Chen et al.*
Patent Abstracts of Japan, Publication No. 05–285000, Publication Date Nov. 2, 1993, 2 pages.
Lee, Myoyong and Walt, David R.; "A Fiber–Optic Microarray Biosensor Using Aptamers as Receptors"; Max Tishler Laboratory for Organic Chemistry, Department of Chemistry, Tufts University, Medford, Massachusetts, Feb. 16, 2000; pp. 142–146.
Walt, David R; "Techview: Molecular Biology, Bead–Based Fiber–Optic Arrays"; Science vol. 287, Jan. 21, 2000, pp. 451–452.
Steemers, Frank J., Ferguson, Jane, A., Walt, David R.; "Screening Unlabeled DNA Targets with Randomly Ordered Fiber–Optic Gene Arrays"; Nature Biotechnology vol. 18; Jan. 2000; pp. 91–94.
Michael, Karri L., Taylor, Laura C., Schultz, Sandra, L., Walt, David R.; "Randomly Ordered Addressable High–Density Optical Sensor Arrays"; Analytical Chemistry, vol. 70, No. 7, Apr. 1, 1998, pp. 1242–1248.
Ferguson, Jane, A., Boles, T. Christian, Adams, Christopher, P., Walt, David, R.; "A Fiber–Optic DNA Biosensor Microarray for the Analysis of Gene Expression" Nature Diotechnology, vol. 14, Dec. 1996, pp. 1681–1684.

* cited by examiner

Primary Examiner—David A. Redding
(74) Attorney, Agent, or Firm—Osha & May, L.L.P.

(57) ABSTRACT

This invention provides a kit used for fabricating an integrated biomolecule sensor. The kit includes an optical fiber bundle unit, which holds the proximal ends of the plurality of optical fibers together with the end-face arranged substantially in the same plane and oriented substantially in the same direction, a plate with wells for holding solutions containing probe polymers with different base sequences, and an auxiliary plate having holes, which corresponds to the wells of the plate respectively. According to this invention, researchers and other people can easily fabricate the integrated biomolecule under individual requirements without need of expensive equipment.

6 Claims, 10 Drawing Sheets

Fig. 10 ical use (U.S. Pat. Nos. 5,744,305 and 5,445,934).

KIT USED FOR FABRICATING AN INTEGRATED BIOMOLECULE SENSOR

CROSS-REFERENCE TO RELATED APPLICATIONS

This application is a divisional application of U.S. patent application Ser. No. 09/962,434, entitled "INTEGRATED BIOMOLECULE SENSOR, METHOD AND APPARATUS FOR FABRICATING THE SENSOR, AND METHOD AND APPARATUS FOR DETECTING BIOMOLECULES USING THE SENSOR," filed Sep. 25, 2001 inventor Hideo Tashiro, et al., and herein incorporated by reference in its entirety.

STATEMENT REGARDING FEDERALLY SPONSORED RESEARCH OR DEVELOPMENT

Not applicable.

BACKGROUND OF INVENTION

1. Field of the Invention

The present invention belongs to the field of biomolecule detection technology that detects a target nucleic acid polymer by using a single-stranded nucleic acid polymer with the base sequence complementary to that of the target nucleic acid polymer to be detected as the probe, allowing a nucleic acid sample obtained from a living body to hybridize to the probe, and detecting the presence of the nucleic acid hybridized to the probe. More specifically, the present invention relates to an integrated biomolecule detection sensor of the bundle type with a plurality of optical fibers held together in an optical fiber bundle unit, the method and apparatus for fabricating the sensor, and the method and apparatus for detecting biomolecules using the sensor.

2. Background Art

DNA microarrays (also referred to as DNA chips) are used as a powerful sensor for detecting biomolecules such as DNA or RNA in samples derived from living bodies. By using DNA microarrays, it is possible to carry out detection or sequencing which requires hundreds to tens of thousands of times of the detection or sequencing operations simultaneously at a time. DNA microarrays have hundreds to tens of thousands of detection points (spots) aligned in rows on a several square centimeters to ten and several square centimeters support made of a glass slide or silicon chip. At each detection point, a single-stranded nucleic acid polymer (gene fragment) with one known base sequence is attached to the support. In other words, DNA microarray is a miniature array of a large number of probe polymers with different base sequences. By applying an aqueous solution of a nucleic acid sample labeled with a fluorophore to such a DNA microarray, only nucleic acid polymers with complementary base sequence hybridize to probes. The DNA microarray is then washed, and only the target nucleic acid polymers hybridized to the probes remain on the DNA microarray. By illuminating with excitation light, fluorescence light is emitted from the fluorophore in the target nucleic acid polymers remaining on the DNA microarray. It can be determined whether there are target nucleic acid polymers present in the nucleic acid sample by detecting the fluorescence light.

DNA microarrays can be divided roughly into the two types according to the fabrication methods: photolithography type and spotting type.

The photolithography-type DNA microarrays are made by synthesizing a large number of DNA (oligonucleotides) with desired different base sequences on a support (chip or sheet) by the photolithography technology used in the fabrication of semiconductor integrated circuits. DNA microarrays with high-density DNA detection points are already put to practical use (U.S. Pat. Nos. 5,744,305 and 5,445,934).

On the other hand, the spotting-type microarrays are made by placing drops containing DNA prepared beforehand one by one on a solid support (U.S. Pat. No. 5,807,522).

The two types of DNA microarrays described above have the following different features.

The photolithography-type DNA microarrays have the advantage of a high measurement sensitivity and its assured reproducibility and being usable for the SNP (Single Nucleotide Polymorphism) analysis because DNA detection points can be made very small and DNA can be grown uniformly. For the fabrication of the photolithography-type of DNA microarrays, an expensive semiconductor manufacturing equipment ("stepper") that costs several million dollars is needed. In addition, the labor and cost for preparing a large number of photomasks increases with the increase of the number of DNA synthesized. The photolithography-type DNA microarrays is therefore very expensive and used only by some research laboratories that have ample research funds as those of pharmaceutical companies at the present time. It is also practically impossible at present to fabricate the photolithography-type DNA microarrays one by one according to the requirements of individual researchers.

The spotting-type microarrays is fabricated by placing drops containing DNA probes on a solid support and drying up, and hence there is inherently a limit to the reduction of the size of DNA detection points. Further, the density and uniformity of the DNA probes attached to the support are not assured so much as they are for the photolithography-type DNA microarrays. This is one of the fundamental factors that prevent the standardization of the spotting-type microarrays. For the fabrication of the spotting-type of DNA microarrays, an expensive, large-scale equipment that costs several tens of millions of dollars is also needed, though not expensive as the equipment for the photolithography-type of DNA microarrays.

SUMMARY OF INVENTION

One of the objects of the present invention is to provide a kit used for fabricating an integrated biomolecule sensor, the kit which researchers and other people can easily fabricate the integrated biomolecule under individual requirements without need of expensive equipment. According to one aspect of one or more embodiments of the present invention, the kit used for fabricating the integrated biomolecule sensor comprises: an holding solutions containing probe polymers with different base sequences; and an auxiliary plate having holes, wherein the respective holes corresponding to the respective wells of the plate.

1. An integrated biomolecule sensor comprising a plurality of optical fibers whose proximal ends are held together with the end-faces arranged substantially in the same plane and oriented substantially in the same direction and which have probe polymers with different base sequences bound to the core end-face at their distal ends.

2. A method of fabricating the integrated biomolecule sensor, comprising the following steps: forming an optical fiber bundle unit by holding the proximal ends of a plurality of optical fibers together with the end-faces arranged substantially in the same plane and oriented substantially in the same direction; and immersing the distal ends of the optical fibers of the optical fiber bundle unit separately in solutions containing probe polymers with different base sequences to let the probe polymer in each solution bind to the core end-face at the distal end of the optical fiber put therein.

3. A method of fabricating the integrated biomolecule sensor, comprising the following steps: forming a number of partial optical fiber bundle units by holding the proximal ends of a plurality of optical fibers together with the end-faces arranged substantially in the same plane and oriented substantially in the same direction; immersing the distal ends of the optical fibers of each of the partial optical fiber bundle units separately in solutions containing probe polymers with different base sequences to let the probe polymer in each solution bind to the core end-face at the distal end of the optical fiber put therein; and joining the partial optical fiber bundle units together into a complete optical fiber bundle unit.

4. The above fabrication method 2 or 3, wherein a linker is bound to the core end-face at the distal end of each optical fiber beforehand and the probe polymers are modified so as to be reactive to bind to the linker.

5. A kit used for fabricating the integrated biomolecule sensor according to the above fabrication method 2 or 3, comprising; a plate with wells for holding solutions containing probe polymers with different base sequences; and an auxiliary plate having holes so arranged in algnment with the wells of the plate as to make it easy to insert the distal ends of individual optical fibers of the optical fiber bundle unit or partial optical fiber bundle units separately into the corresponding different wells of the plate.

6. A method of fabricating the integrated biomolecule sensor, comprising the following steps: forming an optical fiber bundle unit by holding the proximal ends of a plurality of optical fibers together with the end-faces arranged substantially in the same plane and oriented substantially in the same direction; holding the distal ends of the optical fibers of the optical fiber bundle unit in a synthesis vessel; and synthesizing a probe polymer with a desired base sequence on the core end-face at the distal end of each optical fiber by selectively introducing laser light into the optical fibers and supplying solutions of material bases with the photosensitive protecting group bound thereto beforehand into the synthesis vessel in an appropriate order.

7. An apparatus for fabricating the integrated biomolecule sensor, comprising: a synthesis vessel with a valved drain into which solutions of material bases used for synthesizing probe polymers are supplied; mount for supporting the optical fiber bundle unit with the distal ends of the optical fibers kept in the synthesis vessel; synthesis solution supply system for supplying solutions need for the synthesis of probe polymers including solutions of material bases with a photosensitive protecting group bound beforehand into the synthesis vessel; protecting group-dissociating optical system for introducing laser light in the range of wavelengths that can photodissociate the photosensitive protection group from the probe polymers being synthesized into selected one of the optical fibers from the proximal end; moving mechanism for moving said mount for positioning in relation to said protecting group-dissociating optical system: and controller for controlling said synthesis vessel, synthesis solution supply system, protection group-dissociating optical system, and moving mechanism to synthesize a specified probe polymer on the core end-face at the distal end of each optical fiber.

8. A method of detecting biomolecules using the integrated biomolecule sensor, comprising: immersing the distal end of said optical fiber bundle unit in a solution of a nucleic acid sample directly or indirectly labeled with a fluorophore; introducing laser light for exciting fluorescence into selected one of the optical fibers of the optical fiber bundle unit from the proximal; and measuring the intensity of the fluorescence light emitted by the fluorophore in the target polymer hybridized to the probe on the core end-face at the distal end of each optical fiber.

BRIEF DESCRIPTION OF DRAWINGS

FIG. 3 is a schematic representation of the longitudinal sectional structure of each optical fiber of the DNA sensor shown in FIG. 1 and the DNA probe-binding structure for attaching the DNA probe to the core end-face at each optical fiber.

DETAILED DESCRIPTION

Preferred embodiments of the present invention are described below in detail referring to the drawings.

[First Method of Fabricating the DNA Sensor According to the Present Invention]

Figures 1A, 1B:
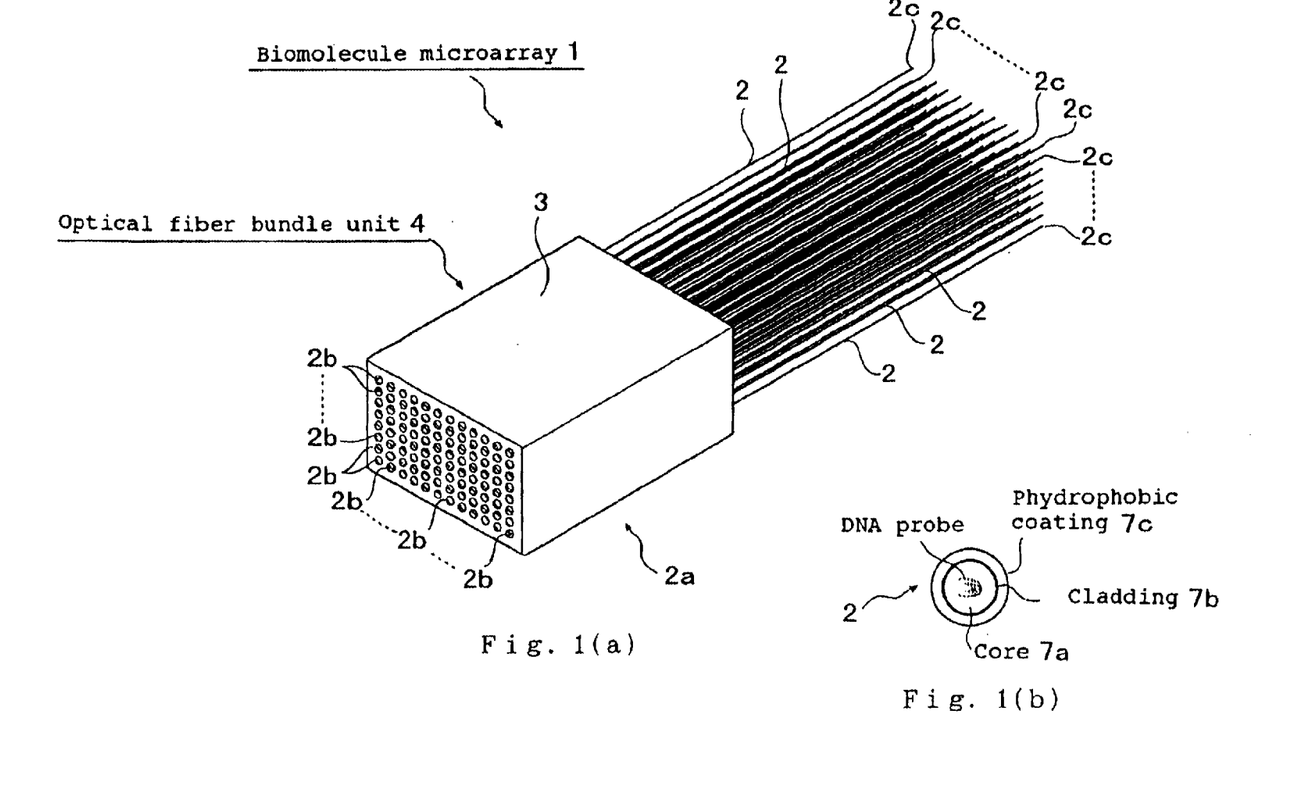
FIG. 1(a) is a perspective view of an integrated DNA sensor as an embodiment of the integrated biomolecule sensor of the present invention.
FIG. 1(b) is a plane view that shows the end-face structure of the optical fibers constituting the DNA sensor show in FIG. 1(a).

FIG. 1(a) is a perspective view of an embodiment of the integrated DNA sensor according to the present invention. FIG. 1(b) shows the end-face structure of the optical fibers constituting the DNA sensor. The DNA sensor 1 has an optical fiber bundle unit 4 formed by holding the proximal ends 2a of 96 same-sized optical fibers together by means of a retainer 3 with the end-faces 2b of the proximal ends arranged substantially in the same plane and oriented substantially in the same direction in a matrix (8×12 rectangular array in this embodiment). DNA probes with different base sequences are bound to the end-face of the core 7a at the distal ends 2c of the individual optical fibers 2 of the optical fiber bundle unit 4.

Figure 2:
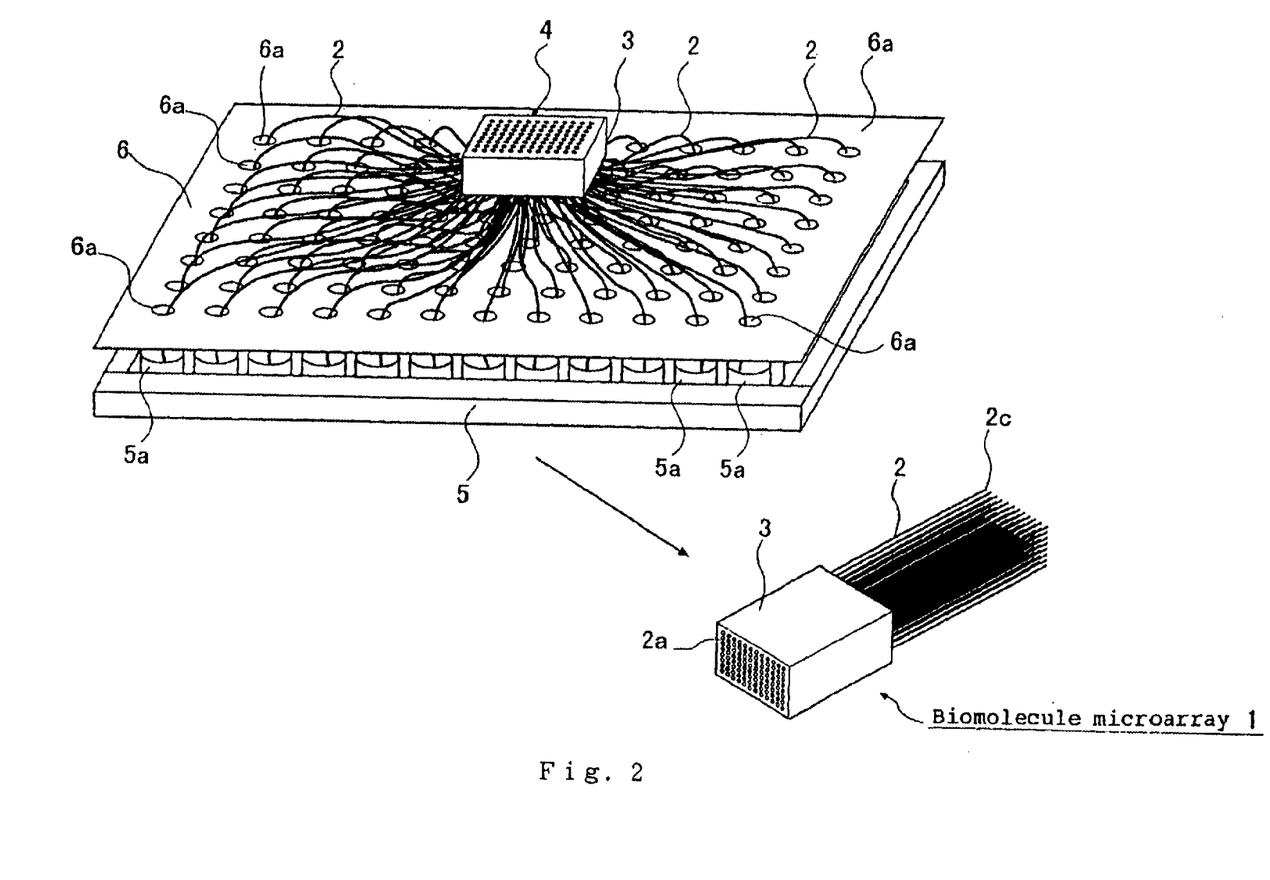
FIG. 2(a) shows a method of making the DNA sensor shown in FIG. 1.

FIG. 2 is a perspective view that illustrates an embodiment of the method of fabricating the DNA sensor 1 shown in FIG. 1. In FIG. 2, designated by reference number 5 is a conventional 96-hole type titer plate having 96 deep wells 5a formed in a matrix (8×12). Designated by reference number 6 is an auxiliary plate for making it easy to insert the optical fibers 2 of the optical fiber bundle unit 4 into their corresponding wells 5a. The auxiliary plate 6 has 96 circular holes 6a with a diameter smaller than the internal diameter of the wells 5a and greater than the external diameter of the optical fibers 2 formed so that the holes 6a are aligned coaxially with the corresponding wells 5a. By passing each of the optical fibers 2 of the optical fiber bundle unit 4 through the corresponding hole 6a of the auxiliary plate 6, the distal ends 2c of the 96 optical fibers 2 of the optical fiber bundle unit 4 can be held apart from each other so that they are positioned just above their corresponding ones of the 96-wells 5a of the titer plate 5.

To fabricate the DNA sensor 1, the 96 wells 5a of the titer plate 5 are filled with solutions of different DNA probes. The optical fibers 2 of the optical fiber bundle unit 4 are passed through their corresponding holes 6a of the auxiliary plate 6, and the distal ends 2c of the optical fibers 2 are inserted into the wells 5a of the titer plate 5 and put into the solutions. While the distal ends 2c of the optical fibers 2 are held in the solutions, the DNA probe in each solution attaches to the end-face of the core 7a of the distal end 2c of the optical fiber 2 held in the solution. The optical fiber bundle unit 4 is then taken off of the titer plate 5, and the distal ends 2c of the optical fibers 2 are dried. Thus made is the DNA sensor 1 with 96 DNA probes attached to the core end-face at the distal ends 2c of the optical fibers 2 of the optical fiber bundle unit 4.

Figure 3A:
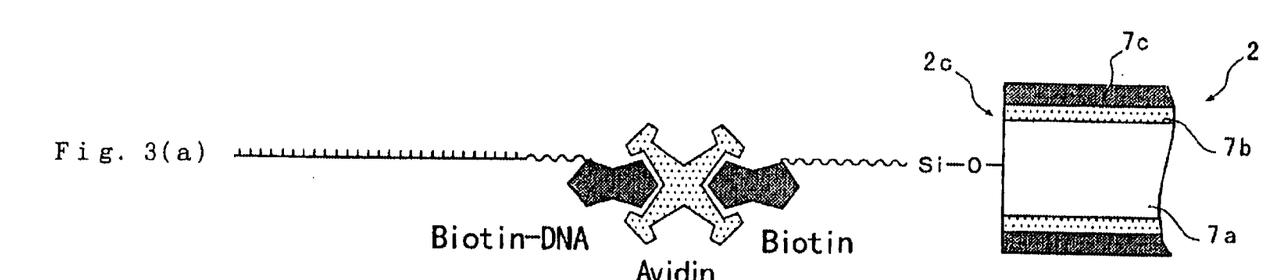
FIG. 3(a) shows an example which binds a biotinylated DNA probe.
Figure 3B:
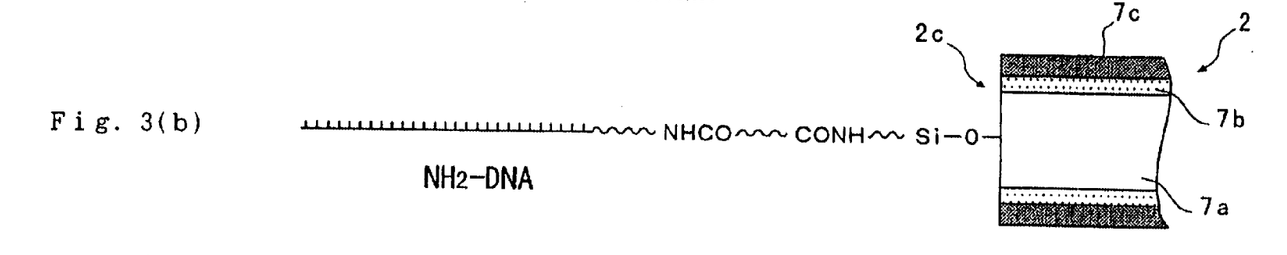
FIG. 3(b) shows an example which binds an amino-linked DNA probe.
Figure 3C:
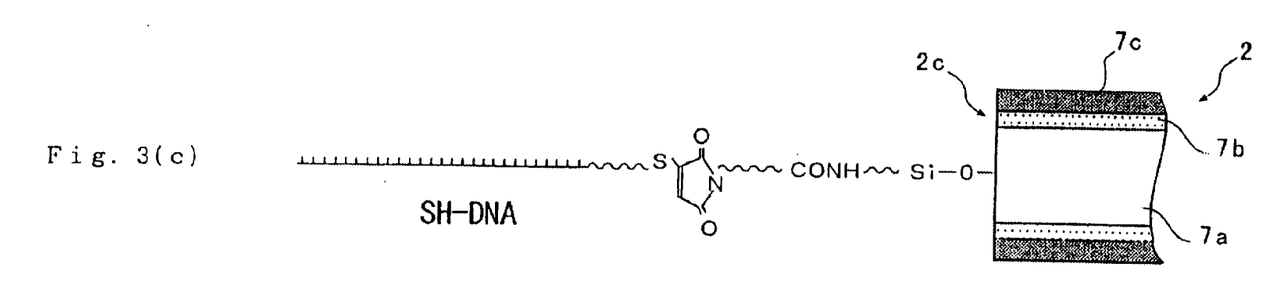
FIG. 3(c) shows an example which binds a thiol-linked DNA probe.

FIGS. 3(a), (b) and (c) are schematic diagrams that show the structure of each optical fiber 2 used for the optical fiber bundle unit 4 and the binding structures of a DNA probe to the end-face of the core.

The optical fiber 2 has the structure in which an inner core 7a is covered with an outer cladding. Further, the outer cladding is covered with a hydrophobic coating 7c. The hydrophobic coating 7c is formed for preventing water from climbing the side surface of the fiber 2 in the hybridization process.

Since the core 7a is made of silica glass, linkers for attaching various DNA probes can be formed to the end-face of the core 7a by using a silane coupling agent. FIG. 3(a) shows an example which attaches a DNA probe to the end-face of an optical fiber by biotin-avidin coupling. In this example, biotin is attached to the end-face of the core 7a and a DNA probe is biotinylated beforehand. The biotin bound to the end-face of the core 7a and that in the DNA probe are linked via avidin. Similarly by forming an appropriate linker on the end-face of the core 7a, it is possible to attach an aminated DNA probe as shown in FIG. 3(b) or a thiolated DNA probe as shown in FIG. 3(c).

Figure 4:
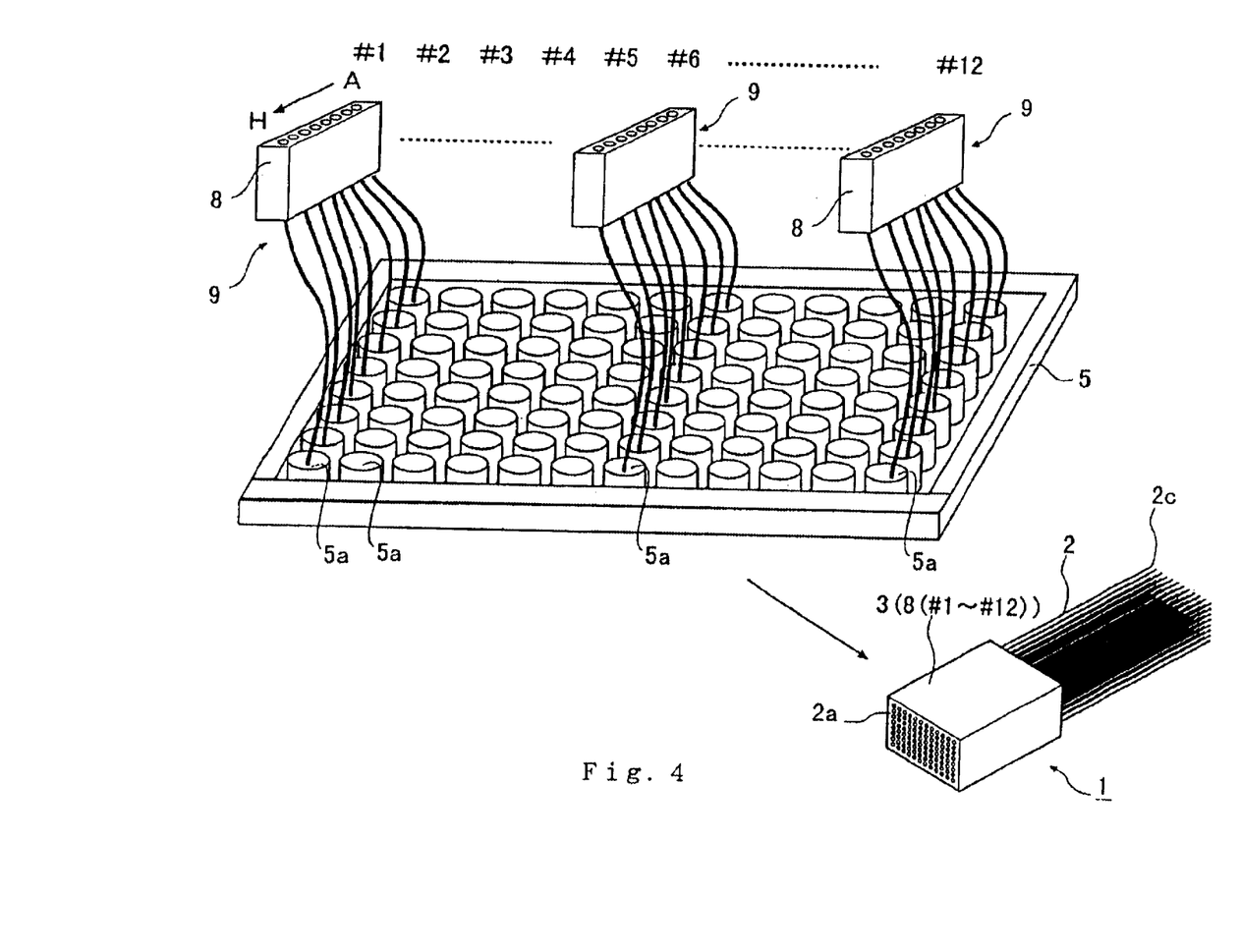
FIG. 4 shows another method of fabricating the DNA sensor shown in FIG. 1.

FIG. 4 shows another method of fabricating the integrated DNA sensor shown in FIG. 1. In this method, 12 optical fiber bundle unit components (#1 to #12), each formed by holding the proximal ends 2a of eight same-sized optical fibers (A to H) 2 together by means of a retainer component 8 with the end-faces 2b aligned in line at the same intervals in the same plane and oriented in the same direction, are first prepared, instead of using an optical fiber bundle unit 4 with 96 optical fibers held together by means of a retainer 3 as used in the fabricating method shown in FIG. 2.

The distal ends 2c of the optical fibers 2 of these 12 optical fiber bundle unit components 9 are inserted into the corresponding wells 5a in the corresponding columns of the 96-well titer plate 5 and immersed in the solutions to let the DNA probe in each solution attach to the core end-face at the distal end 2c in the solution, and then taken out of the wells. After the distal ends 2c of the optical fibers are dried, the retainer components 8 of the 12 optical fiber bundle unit components 9 are put together and joined. Thus made is the DNA sensor 1.

Figure 5:
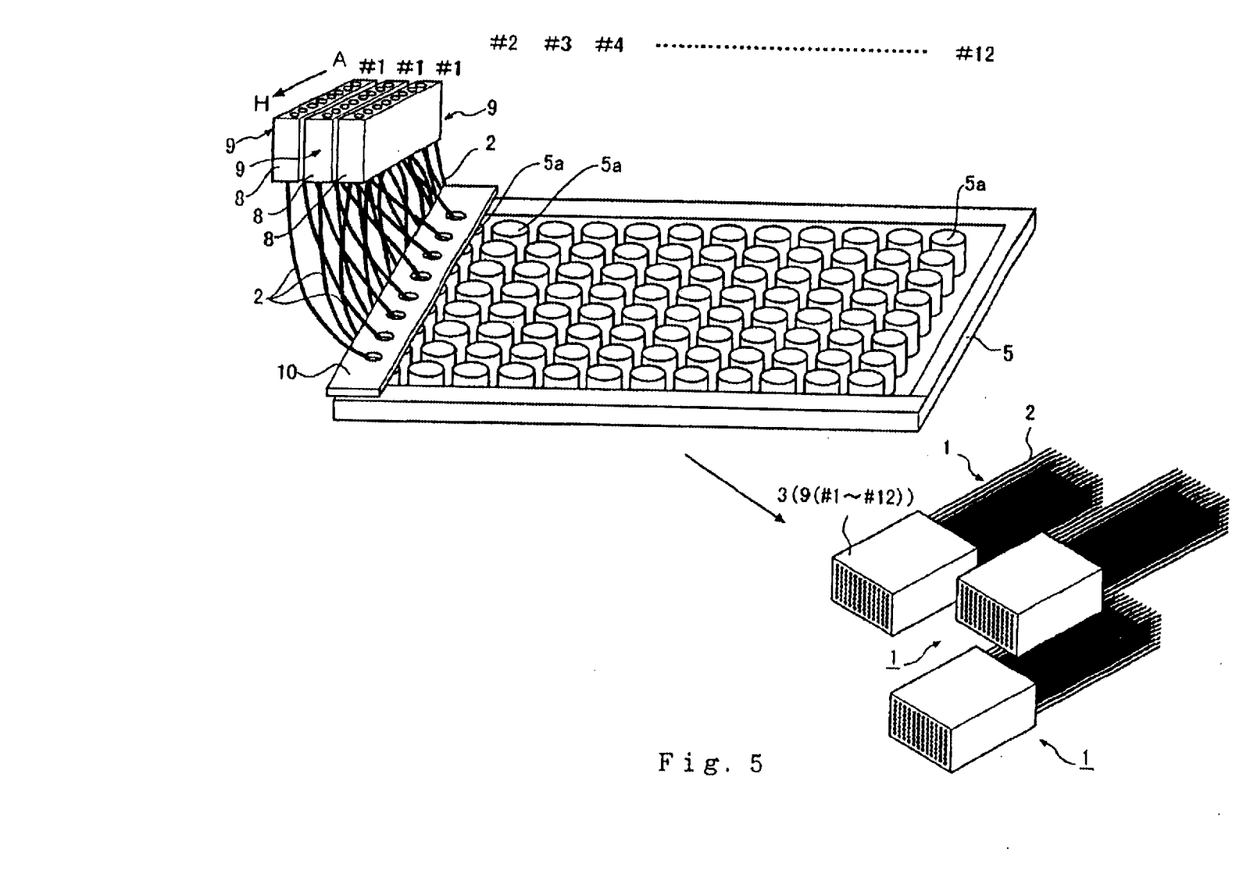
FIG. 5 shows another method of fabricating the DNA sensor shown in FIG. 1.

Further, the probe-attaching operation may be performed by dipping the distal ends 2c of the optical fibers 2 of the optical fiber bundle unit components 9 with the same unit component number for two or more, e.g. three, DNA sensors in the wells 5a in one column of the 96-well titer plate 5 column by column, in the manner as shown in FIG. 5. After the probe-attaching operation, the 12 optical fiber bundle unit components 9 for each DNA sensor are collected and their retainer components 8 are joined together. It is therefore possible to make two or more DNA sensors 1 simultaneously. Use of an auxiliary plate 10 as shown in FIG. 5 makes easy the work of inserting a plurality of the distal ends 2c of the optical fibers 2 into the same well 5a of the titer plate 5.

Figure 6:
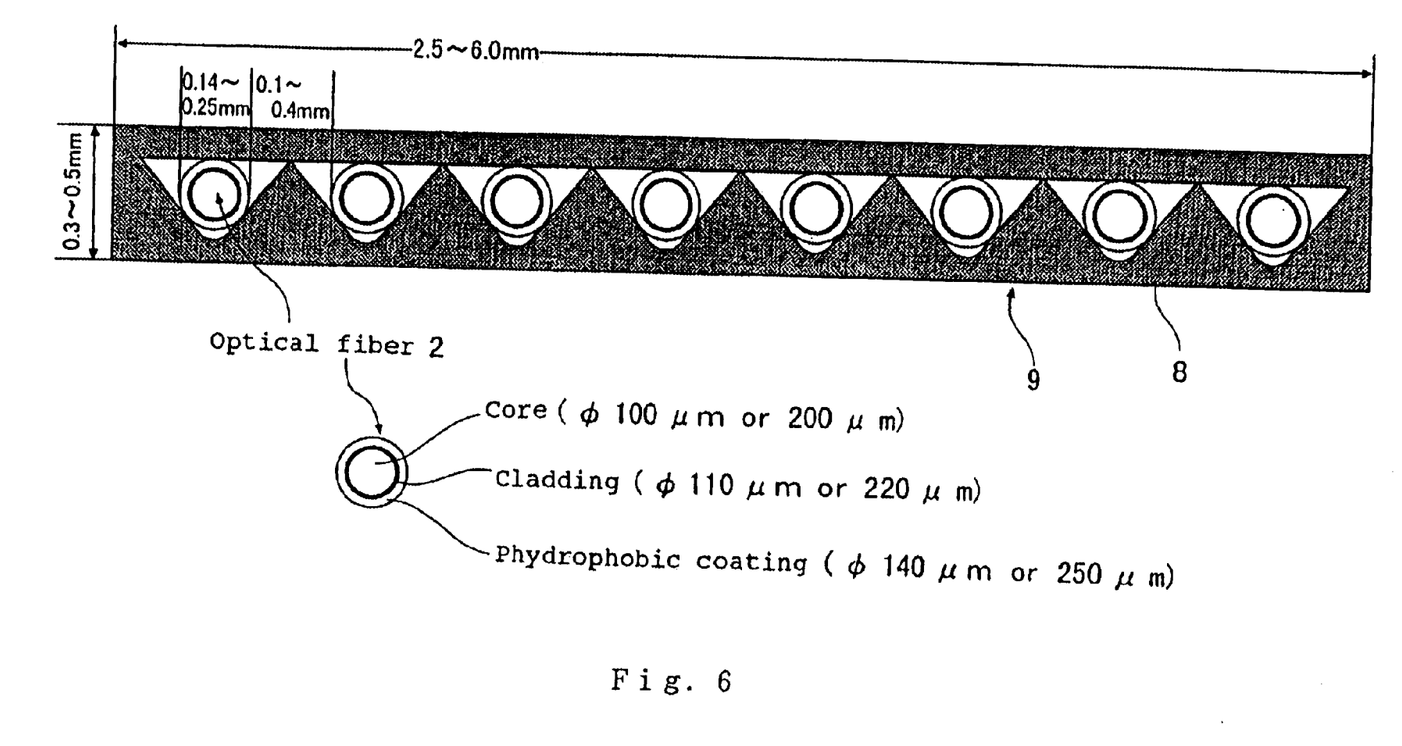
FIG. 6 shows an example of the cross-sectional structure of the retainer component.
Figure 7:
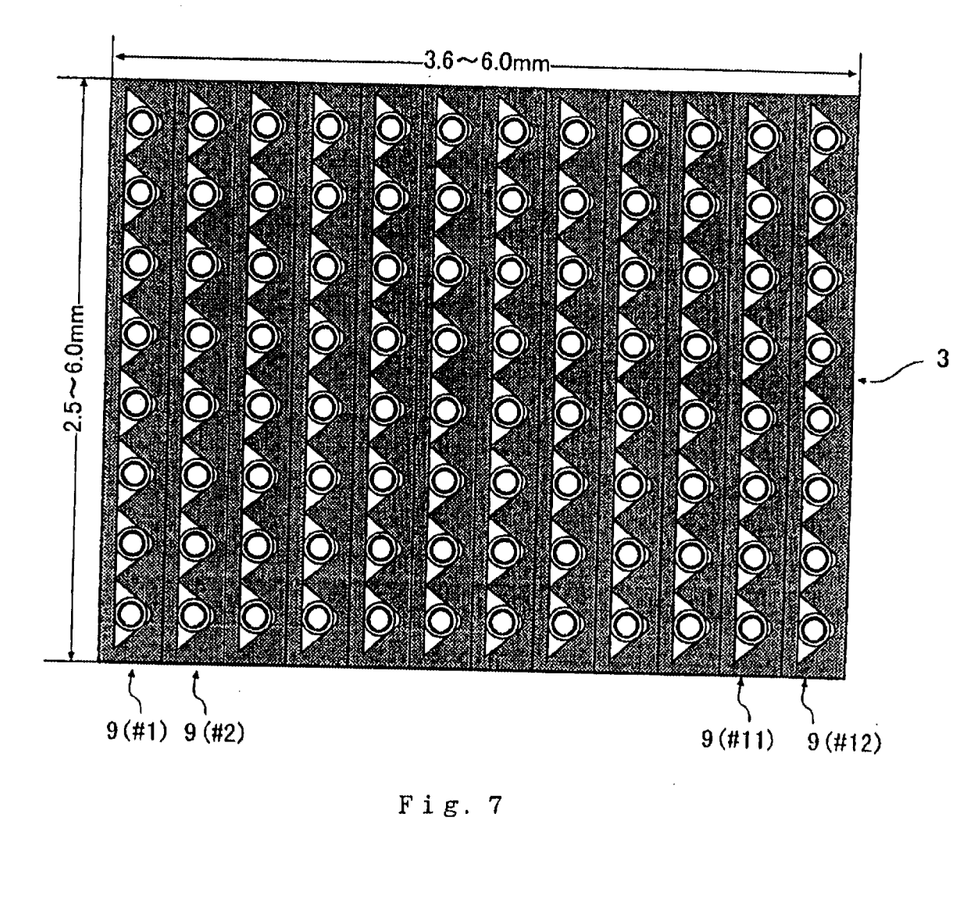
FIG. 7 shows the cross-sectional structure of the retainer formed by 12 retainer components joined together.

The retainer components 8 are made of zirconia, silica glass, silicone or a plastic. They are joined together with an adhesive agent or any other means such as screws. Twelve retainer components 8 joined together makes the same retainer as the retainer 3 shown in FIGS. 1 and 2 in functions and structure. FIG. 6 shows an example of the cross-sectional structure of the retainer component 8, and FIG. 7 shows the cross-sectional structure of the retainer 3 formed by 12 retainer components 8 joined together. The dimensions in FIGS. 6 and 7 are shown by way of example, not for limiting the scope of the invention.

According to the method described above, one DNA probe is attached to the end-face of the core 7a at the distal end 2c of each optical fiber 2 by immersing the distal end 2c of each optical fiber 2 in a solution containing one DNA probe. Thus it is made possible to attach any desired DNA probe uniformly to the end-face of the core 7a at the distal end 2c of each optical fiber 2, handling the optical fibers 2 to attach different DNA probes to completly separately. Therefore, by using this method, researchers can easily make integrated biomolecule detection sensors suited for their research purposes for themselves without need of a costly fabricating apparatus such as a spotting-type arrayer.

Further, in the above method, a DNA probe can be attached to the end-face of the core 7a of each optical fiber 2 in a solution by the solid phase—bulk solution reaction. Therefore, the reproducibility of the reaction conditions improves in comparison with that of the conventional method of attaching DNA probes on a solid support (sheet) by the solid phase—spot solution (liquid drop) reaction. Accordingly, the DNA sensor 1 made by this method can be easily standardized.

[Second Method of Fabricating the DNA Sensor of the Present Invention]

Figure 8:
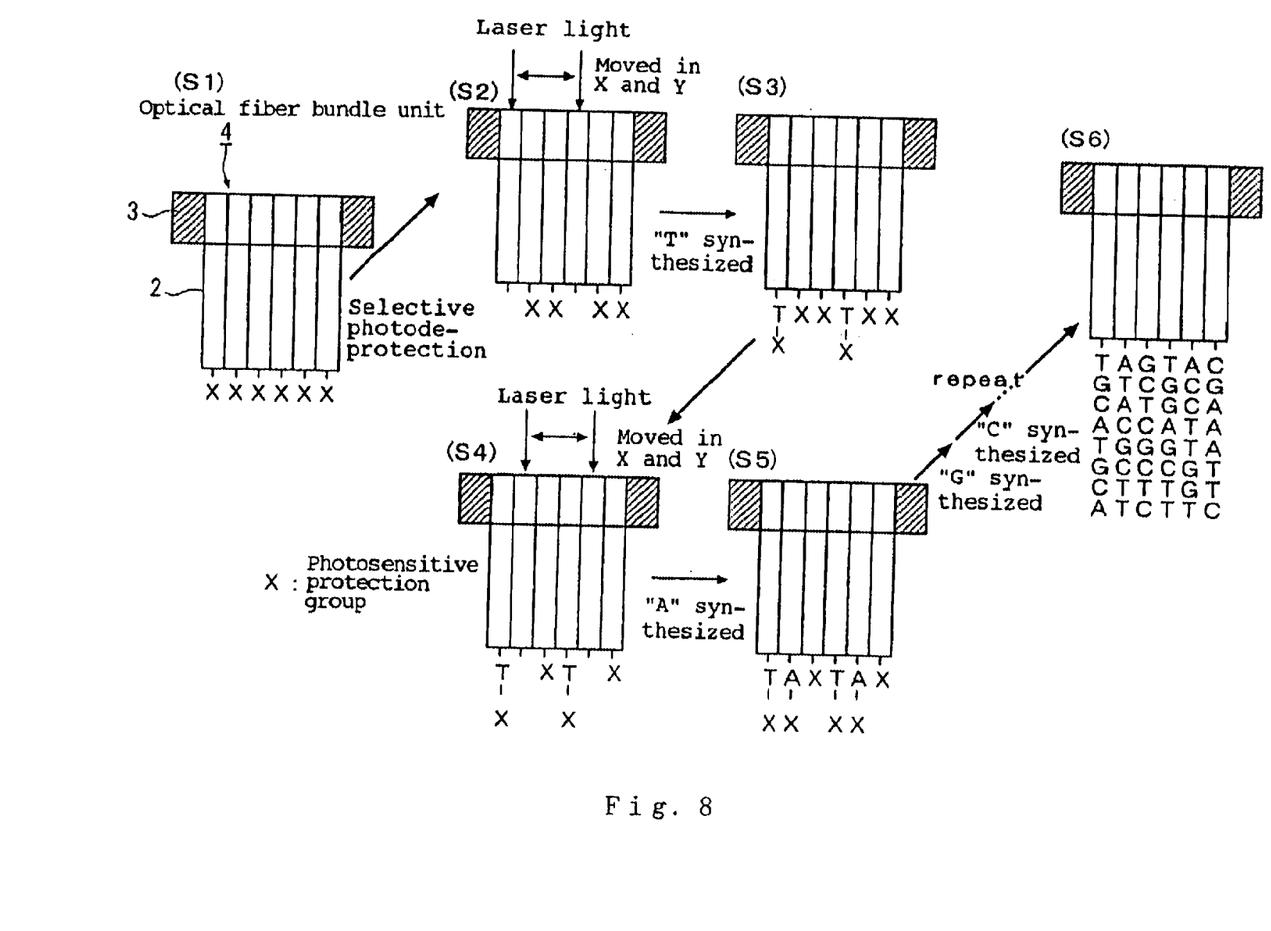
FIG. 8 is a schematic representation of the process of another method of fabricating the DNA sensor of FIG. 1.

FIG. 8 is a schematic representation of the process of another method of fabricating the DNA sensor 1 shown in FIG. 1. The configuration of the optical fiber bundle unit 4 in FIG. 8 is the same as that shown in FIG. 1, but it is diagrammatically shown in FIG. 8.

A photosensitive protecting group X is attached to the end-face of the core 7a at the distal end of each optical fiber 2 of the optical fiber bundle unit 4 with an appropriate intermediate linker beforehand (Step S1).

The photosensitive protecting group X is released from the optical fibers 2 to which a first material base is to be bounded (the first and fourth optical fibers from the left in this example) by introducing laser light into those optical fibers from their proximal ends, putting the distal end of the optical fiber bundle unit 4 in an organic solvent or a low-reactivity gas such as argon, helium, or nitrogen (Step 2).

Next, the binding reactivity of a material base is activated by mixing solutions of a material base and an activator. The distal end of the optical fiber bundle unit 4 is immersed in the mixed solution, allowing the material base (T(thymine) in this example) to bind to the end of the molecules from which the photosensitive protecting group x has been removed (Step 3). The photosensitive protecting group X is bound to the material base beforehand.

When binding another material base to other optical fibers 2, laser light is introduced into the optical fibers (the second and fifth optical fibers from the left in this example) from the end-face at the proximal end 2a to release the photosensitive protecting group X in the same manner as in step 2 (Step 4). Next, the distal end of the optical fiber bundle unit 4 is immersed in a solution containing the activated material base (A(adenine) in this example) to allow the material base bind to the end of the molecules from which the photosensitive protecting group X has been removed (Step 5).

By repeating the above described steps which introduce laser light into the optical fibers to which a material base is to be bound to release the photosensitive protecting group X and then let the material base bind to the ends of the molecules from which the photosensitive protecting group X has been removed, a DNA probe (oligonucleotide) with any desired base sequence can be synthesized (Step 6).

The photosensitive protecting group X bound to the ends of the synthesized DNA probes and other protecting groups in the probes such as protecting groups bound to the bases and phosphate groups are then removed with a deprotecting agent. Finally, the distal ends 2c of the optical fibers are dried. Thus made is the DNA sensor 1.

[Fabricating Apparatus]

Figure 9:
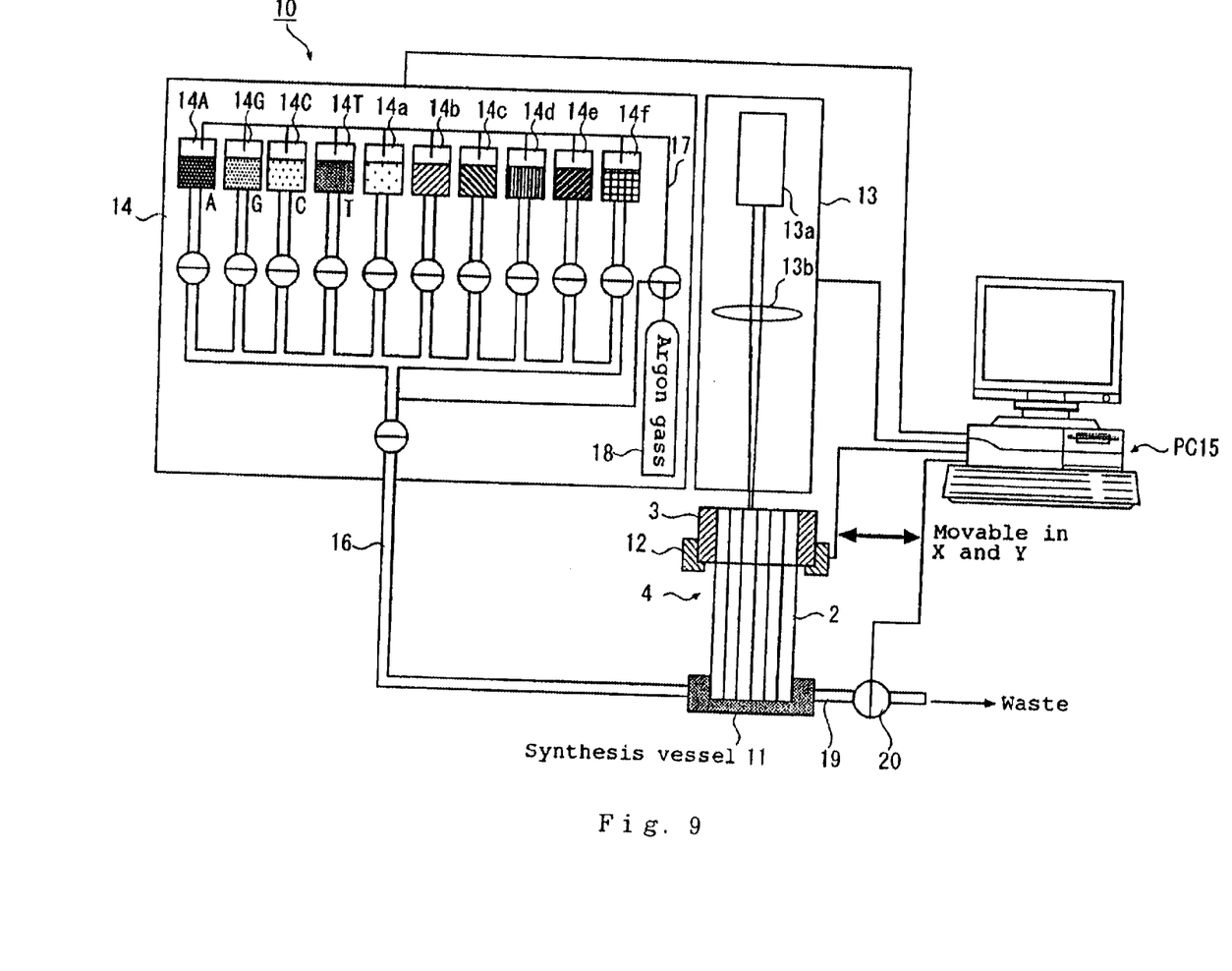
FIG. 9 shows a schematic representation of an embodiment of the apparatus for fabricating the DNA sensor of FIG. 1 using the method illustrated in FIG. 8.

FIG. 9 shows a schematic representation of an embodiment of the apparatus for fabricating the DNA sensor 1 using the method illustrated in FIG. 8.

The apparatus 10 comprises a synthesis vessel 11, mount 12 that holds the retainer 3 horizontal with the distal ends of the optical fibers of the optical fiber bundle unit 4 down keeping the distal ends in the synthesis vessel 11, protecting group-releasing optical system 13 that generates a laser light beam and focuses the laser light beam onto the end-face of the core 7a of one optical fiber, synthesis solution supply system 14 that supplies solutions containing material bases and other substances in the synthesis vessel 11, moving mechanism (not shown) that moves the retainer 12 in the X and Y directions (horizontal direction), and personal computer (PC) 15 as the controller for controlling the entire fabricating apparatus 10.

The protecting group-releasing optical system 13 comprises a laser light source 13a that generates laser light in the ultraviolet range and a lens 13b that focuses the laser light from the laser light source 13a onto the end-face of the core 7a of one optical fiber 2.

The synthesis solution supply system 14 comprises four material base solution vessels 14A, 14T, 14G, and 14C that hold solutions containing A (adenine), T (thymine), G (guanine), and C (cytosine), respectively and other solution vessels including the oxydizing agent vessel 14a, deprotecting agent vessel 14b, washing solvent vessel 14c, activator vessel 14d, capping agent vessel 14e, and solvent vessel 14f, etc. Each solution vessel is connected to the synthesis vessel 11 through solution supply piping 16. The upper part of each solution vessel is connected to a supply source 18 of a compressed low-reactivity gas (argon in this embodiment) for forcing supply of the solutions, through a gas supply piping 17. The solution supply piping 16 is provided with a valve for each solution vessel. The solutions in the synthesis solution supply system 14 can be selectively supplied into the synthesis vessel 11 in necessary amounts by opening the valve for the solution vessel holding the solution and the valve in the gas supply piping 17.

The PC 15 has a base sequence synthesizing program installed. It controls the laser light source 13a in the protecting group-releasing optical system 13, the valves in the synthesis solution supply system 14 to open or close them, the moving mechanism (not shown) for positioning a selected optical fiber at the position where the laser light is introduced into the optical fiber, and the valve 20 in the drain pipe 19 of the synthesis vessel 11 to open or close it, to synthesize a DNA probe with the specified base sequence on the end-face of the core 7a at the distal end of each optical fiber 2 of the optical fiber bundle unit 4, by the fabricating method described above, according to the information input by the operator such as the address of each optical fiber of the optical fiber bundle unit (positional information) and the base sequence of the DNA probe to be formed for the optical fiber at each address.

To explain the operation of the apparatus more specifically, (1) When letting a material base bind to the molecules on the end-faces of desired optical fibers 2, the synthesis vessel 11 is filled with the solvent or the gas (argon), laser light (ultraviolet light) is introduced into the optical fibers to release the photosensitive protecting group X, and the synthesis vessel 11 is washed with the washing solvent.

(2) The material base is activated with the activator and then filled into the synthesis vessel 11 to let the material base bind to the end of the linker or synthesized molecules from which the photosensitive protecting group X is released. Subsequently, the synthesis vessel 11 is washed with the washing solvent.

(3) The phosphoric acid is oxydized with the oxydizing agent. The synthesis vessel 11 is subsequently washed with the washing solvent.

(4) The capping agent is supplied into the synthesis vessel 11 to cap the unreacted end-face of the fibers. After the capping is completed, the synthesis vessel 11 is washed with the washing solvent.

The operation of steps (1) to (4) above constitute the synthesizing cycle for adding one base. This synthesizing cycle is repeated until all DNA probes with desired base sequences are synthesized. After all DNA probes are synthesized, the deprotecting agent is supplied into the synthesis vessel 11 to release the photosensitive protecting group X bound to the end of the DNA probes and the protecting groups X bound to the bases and phosphate groups in the DNA probes.

Finally, the optical fiber bundle unit 4 is taken down from the mount 12 and dried. Thus made is the DNA sensor 1 that has 96 different DNA probes attached to the core end-face at the distal end 2c of the 96 optical fibers 2.

By this fabricating method and apparatus, as described above, a DNA probe with any desired base sequence can be synthesized on the end-face of each optical fiber 2 by supplying solutions including those of material bases with a photosensitive protecting group X bound to them, oxydizing agent, deprotecting agent, washing solvent, activator, capping agent and solvent into the synthesis vessel 11 in an appropriate order, keeping the distal ends 2c of the optical fibers 2 in the synthesis vessel 11 and introducing laser light into the optical fibers for which the next material base is supplied. Further, a large number of DNA probes with different base sequences can be synthesized efficiently and automatically by computer control using the technique of combinatorial chemistry. This fabricating method and apparatus therefore can be used for fabricating DNA sensors for SNP typing which needs a large number of DNA probes slightly different in their base sequences.

[Method and Apparatus for Detecting Biomolecules]

Next, the method and apparatus for detecting the target nucleic acid polymers in a nucleic acid sample using the DNA sensor 1 fabricated as described above are described below.

Figure 10:
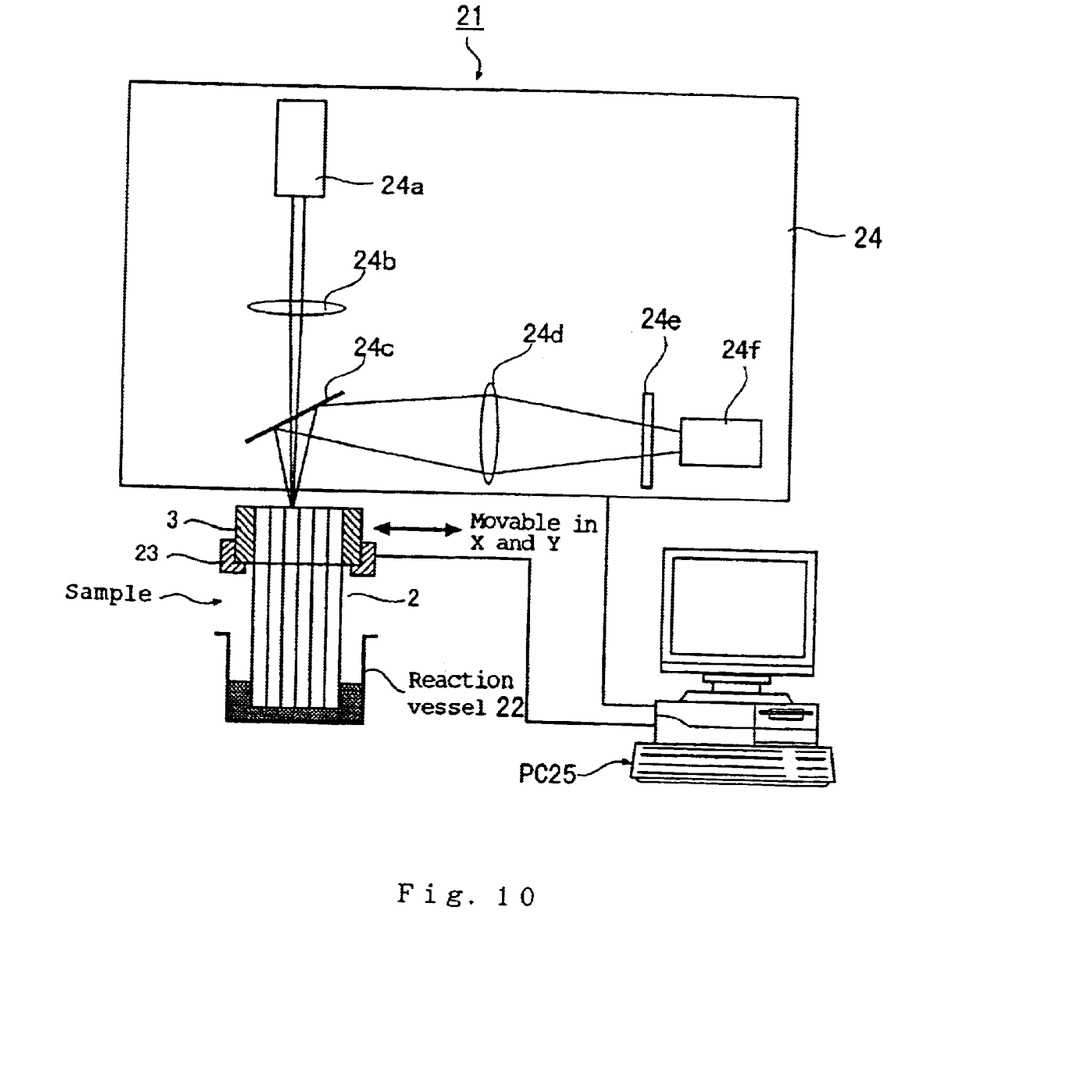
FIG. 10 is a schematic representation of an embodiment of the biomolecule detection apparatus according to the present invention.

FIG. 10 is a schematic representation of an embodiment of the biomolecule detection apparatus according to the present invention.

The biomolecule detection apparatus 21 comprises a reaction vessel 22 for holding the solution of sample nucleic acids, mount 23 for supporting the retainer 3 of the DNA sensor 1 horizontally with the distal ends 2c of the optical fibers down kept in the hybridizing vessel 22, fluorescence detection optical system 24 for introducing laser light for exciting fluorescence into one optical fiber 2 of the DNA sensor 1 from the proximal end 2a selectively and detecting the fluorescence light coming back through the optical fiber 2, mount-moving mechanism (not shown) for moving the mount horizontally in the X and Y directions for positioning, and personal computer (PC) 25 as the controller for controlling the entire apparatus.

The fluorescence detection optical system 24 comprises a laser light source 24a for generating laser light of a specific wavelength for exciting the fluorochrome labeled nucleic acid sample, lenses 24b for focusing the laser light from the laser light source 24a onto the end-face of the core 7a of one optical fiber 2 of the DNA sensor 1 held by the mount 23, dichroic mirror 24c for reflecting the fluorescence light coming back out of the optical fiber 2 at approximately right angles, lenses 24d for focusing the light reflected from the dichroic mirror 24c, filter 24e for allowing only the wavelength of the fluorescence by the fluorochrome to pass, and photosensor 24f for detecting the light passing through the filter 24e. For the photosensor 24f, a photomultiplier or CCD (Charge Coupled Device), for example, can be used.

The PC 25 has a detection program for detecting the target nucleic acid polymers in sample nucleic acid solutions using the DNA sensor 1 installed. The detection program controls the operation of the laser light source 24a in the fluorescence detection optical system 24 and the position of the mount 12 in the X and Y directions by the moving mechanism not shown to introduce laser light into the optical fibers 2 one by one and read in the intensity of the fluorescence light from each optical fiber 2 detected by the photosensor 24.

To detect the target nucleic acid polymers in sample nucleic acids, the solution of the sample nucleic acids is put in the reaction vessel 22, the DNA sensor 1 is put on the mount 23, and the distal ends of the optical fibers 2 are immersed in the solution in the reaction vessel 22. This allows the target nucleic acids to hybridize to the DNA probe on the end-face of the core 7a of the distal end of each optical fiber 2.

The detection program described above is then executed on the PC 25. The program introduces laser light into each optical fiber 2 of the DNA sensor 1 one by one, and the measurement of the intensity of the fluorescence light coming back through each optical fiber 2 is performed automatically. The results are displayed on the monitor and stored in the storage of the PC 25, and can be printed out. The presence of 96 nucleic acid polymers in the sample can be determined according to the results.

By this detecting method and apparatus, it is possible to perform fluorescence observations letting hybridization reaction of the DNA probes on the distal ends of the optical fibers and sample nucleic acid polymers occur with the distal ends of the optical fibers immersed in a sample nucleic acid solution. it is therefore made possible to speed up the hybridaization reaction and perform the fluorescence observations in real time.

Further, by this detection method and apparatus, detection of target nucleic acid polymers is performed by introducing laser light into the optical fibers 2 of the DNA sensor 1 one by one and measuring the fluorescence light coming back through each optical fiber. Therefore, an optical system with a fine spatial resolution, as needed when using conventional DNA microarrays made by arranging DNA detection points (spots) on supports such as glass plates or silicon chips, is not needed. The detection apparatus therefore can be simplified and made at a lower cost.

Further, the DNA sensor 1 used for the detection can be fabricated by immersing the distal ends 2c of the optical fibers 2 of the optical fiber bundle unit 4 in the solutions of different DNA probes and thereby attaching the DNA probe in each solution to the end-face of the optical fiber 2 in the solution. No expensive fabricating apparatus is therefore not required, and researchers can easily make DNA sensors which best suit individual requirements.

After the DNA sensor 1 is used for the detection of target nucleic acids, the nucleic acids hybridized to the DNA probes can be released from the DNA probes by immersing the distal ends of the optical fibers in a nucleic acid-denaturing solution such as formaldehyde solution. The DNA sensor 1 therefore can be used repeatedly. Further, the DNA probes attached to the end-face of the optical fibers can also be released by immersing the distal ends of the optical fibers in an appropriate solution. In the case in which DNA probes are attached to the end-faces of the optical fibers by biotin-avidin coupling, for example, the DNA probes can be released by immersing the distal ends of the optical fibers in a guanidine hydrochloride solution, the optical fiber bundle unit 4 can also be used repeatedly.

The scope of the present invention is not limited to the embodiments described above.

Although a DNA sensor with DNA polymers bound to the end-face of the core 7a of the optical fibers 2 as the probe polymers is shown as an embodiment of the integrated biomolecule sensor according to the present invention, sensors using RNA, PNA, protein as the probe polymers are also included in the integrated biomolecule sensor according to the present invention.

Further, although the integrated biomolecule sensors described above have an optical fiber bundle unit formed of 96 optical fibers held together, the number of the optical fibers for constituting the optical fiber bundle unit is not limited to 96. It is possible to put the integrated biomolecule sensor using an optical fiber bundle unit formed of thousands to tens of thousands of optical fibers into practice by increasing the integration degree of the optical fiber bundle unit.

The arrangement of the optical fibers in the optical fiber bundle unit is not limited to an 8.times.12 rectangular array as used in the integrated biomolecule sensors described above, but may be any other arrangement such as a circular arrangement. Therefore, the shape of the retainer is not limited to a rectangular parallelepiped, but may be a cylinder or any other shape.

The optical fiber bundle unit may also be held together by means of a retainer or retainers at any position(s) in addition to the proximal end portion.

Further, although the biomolecule detection apparatus described above has a configuration which measures light coming back through the optical fibers, it is also possible to use a transparent reaction vessel and measure the fluorescence light from the distal ends of the optical fibers through the wall of the reaction vessel.

As known from the above description, the present invention has the following merits:

The integrated biomolecule sensor of the present invention makes it possible for researchers to make their own sensors according to individual requirements without need of expensive equipment.

By the method, apparatus and kit for fabricating the integrated biomolecule sensor of the present invention, it is made possible for researchers to make their own sensors according to individual requirements without need of expensive equipment.

Further, by the biomolecule-detecting method and apparatus of the present invention, it is also made possible to detect target nucleic acid polymers in nucleic acid samples by a simpler and lower-cost apparatus than conventional apparatuses, using the integrated biomolecule sensor of the present invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A kit used for fabricating an integrated biomolecule sensor, comprising:

an optical fiber bundle unit, which comprises a plurality of optical fibers held together at proximal ends in an ordered array with end-faces arranged substantially in the same plane and oriented substantially in the same direction, wherein core end-faces at one end of the plurality of optical fibers are configured to attach probe polymers;

a plate with wells for holding solutions containing the probe polymers in an ordered array; and an auxiliary plate, which can be detachably fitted on top of the plate and has holes aligned with the corresponding wells of the plate for passing distal ends of the plurality of optical fibers therethrough into the wells.

2. The kit according to claim 1, wherein the optical fiber bundle unit further comprises a linker bound to the distal end of each optical fiber thereof.

3. A kit used for fabricating an integrated biomolecule sensor, comprising:

a plurality of partial optical fiber bundle units, each of which comprises a plurality of optical fibers held together at proximal ends with end-faces arranged substantially in the same plane and oriented substantially in the same direction and which can be joined together to form a complete sensor, wherein core end-faces at one end of the plurality of optical fibers are configured to attach probe polymers;

a plate with wells for holding solutions containing the probe polymers in an ordered array; and an auxiliary plate, which can be detachably fitted on top of the plate and has holes aligned with the corresponding wells of the plate for passing distal ends of the plurality of optical fibers therethrough into the wells.

4. The kit of claim 3, wherein the auxiliary plate has a width to cover a row of wells of the plate and has holes disposed in line aligned with the corresponding wells of the plate to facilitate insertion of the distal ends of the plurality of optical fibers into the wells.

5. The kit of claim 3, wherein the partial optical fiber bundle unit further comprises a linker bound to the distal end of each optical fiber.

6. The kit of claim 4, wherein the partial optical fiber bundle unit further comprises a linker bound to the distal end of each optical fiber.

* * * * *